United States Patent [19]

Osada et al.

[11] Patent Number: 5,686,636

[45] Date of Patent: Nov. 11, 1997

[54] PROCESS FOR PREPARING HIGH-PURITY CHOLESTEROL

[75] Inventors: Takeshi Osada; Katsunori Myojyo, both of Takasago, Japan

[73] Assignee: Nippon Fine Chemical Co., Ltd., Osaka, Japan

[21] Appl. No.: 505,191

[22] PCT Filed: Dec. 16, 1993

[86] PCT No.: PCT/JP93/01823

§ 371 Date: Aug. 14, 1995

§ 102(e) Date: Aug. 14, 1995

[87] PCT Pub. No.: WO95/16700

PCT Pub. Date: Jun. 22, 1995

[51] Int. Cl.⁶ ................................................ C07J 9/00
[52] U.S. Cl. ................................................ 552/544
[58] Field of Search ................................ 552/544

[56] References Cited

PUBLICATIONS

Patent Abstract of Japan—01–117897 A, May 10, 1989.
Patent Abstract of Japan—62–277396 A, Dec. 2, 1987.
J. of Lipid Research; vol. 20, No. 1, Jan. 1979; pp. 134–139; Bentzen C.L. et al.—"Synthesis of [24,25–3H]–cholesterol: a new substrate . . . ".
Journal of Organic chem., vol. 47, No. 9, 23 Apr. 1982, pp. 1722–1724; H. Kircher et al.—"Preparation of Some Unsaturated . . . ".
Journal of Organic Chem., vol. 52, No. 12; 12 Jun. 1987, pp. 2586–2588; H. Kircher et al.—"Preparation of Desmosterol from . . . ".
Progr. Biochem. Pharmacol.; vol. 5 (1969), pp. 24–34; Frantz I.D.; "Synthesis and use of labeled sterols". p. 29, paragraph 5.
Chemical Abstract, vol. 119, No. 6; 9 Aug. 1993, Abstract No. 51730 Lauko et al.; "Analysis of Steroids, Part 46 . . . ".
Chemical Abstract, vol. 76, No. 3; 17 Jan. 1972, Abstract No. 011352 Watkinson et al.; "Substrate activation in some pyridine nucleotide . . . ".
Journal of Chem. Soc., Chem. Commun., No. 10, 15 May 1991, Letchworth, GB pp. 688–689; Fujimoto, Y. et al.—"Stereochemistry of the hydrogen . . . ".
Journal of the American Chem. Society, vol. 95, No. 6; 21 Mar. 1973, DC; pp. 1996–2001; M.G. Kienle et al.—"Reduction of delta–24 Lanosterol . . . ".
Chem. Abs 105:94971 (1985).

Primary Examiner—Paul J. Killos
Attorney, Agent, or Firm—Armstrong, Westerman, Hattori, McLeland & Naughton

[57] ABSTRACT

The invention provides a process for preparing high-purity cholesterol, the process comprising selectively reducing the impurities (mainly desmosterol) contained in a crude cholesterol to cholesterol.

According to the invention, high-purity cholesterol can be obtained in a yield of at least 85%, the cholesterol containing 0.3% or less of desmosterol, 0.5% or less of dihydrocholesterol and having a purity of at least 99% after reduction and crystallization.

3 Claims, No Drawings

PROCESS FOR PREPARING HIGH-PURITY CHOLESTEROL

This application is a 371 of PCT/JP93/01823 filed Dec. 16, 1993.

FIELD OF THE INVENTION

The present invention relates to a process for preparing high-purity cholesterol from impurities-containing crude cholesterol by selective reduction of said impurities to cholesterol.

PRIOR ART

The cholesterol widely used in the fields of medicines, cosmetics and livestock feeds is produced from wool grease, fish oils or brains of higher animals, and mostly from wool grease.

Known processes for preparing cholesterol from wool grease include a solvent extraction based on a difference in solubility, an adduct method utilizing a low solubility of an adduct of cholesterol with a metal, column chromatography, etc. However, since these methods, if practiced singly, fail to produce fully purified products, currently the cholesterol prepared by each method is concentrated and finally recrystallized to improve the purity.

The purity of said cholesterol is specified as equivalent to a melting point of 147° to 150° C. in the Japanese Pharmacopoeia and in the U.S. NF. Commercially available cholesterols (24 samples) have a purity in the range of 90.7 to 96.3% as determined by assay through GLC.

In recent years, researches have been actively conducted on drug delivery system in the medical field. Currently investigations are being made into, as one of the system means, liposomes having a medicament covered with a membrane composed of phospholipid and cholesterol. In this connection, the purity of cholesterol useful as the starting material has come into question. And now there is an increased need for cholesterol of higher purity. Similarly as to cholesterol for use as materials for synthesis of pharmaceuticals or as reagents for biochemical research, the currently acceptable purity levels are now considered unsatisfactory. Consequently there is an increasingly strong demand for cholesterol of higher purity.

To improve the purity of cholesterol by conventional methods, repeated recrystallization is done. However, this way can not improve the purity and yield concurrently. For example, when recrystallization is repeated three times using a 95.5%-pure commercially available cholesterol as the starting cholesterol, the purity is increased to 98.8%, but the yield is markedly lowered to 42%. Thus this is not practical.

In view of such status of art, an object of the present invention is to provide a process for preparing cholesterol with a high purity in a high yield.

To achieve the above object, the inventors of the present invention assayed commercially available cholesterols (hereinafter "commercial cholesterol") by GLC and found that they had a purity of 90.7 to 96.3%. The commercial cholesterols were also found to contain 5.1 to 2.6% desmosterol, as a main contaminant, having double bonds in the 5-position of the sterol skeleton and in the 24-position of the side chain. It was confirmed that the desmosterol can not be removed, except little by little, by recrystallization.

The inventors carried out further extensive investigations, directing attention to the desmosterol as a major contaminant, and found that the desmosterol is converted to cholesterol by the reduction of the double bond in the side chain of desmosterol. More specifically, the inventors found not only that the desmosterol can be converted to cholesterol but also that cholesterol can be obtained with a high purity and in a high yield by a selective reduction method substantially free of loss of cholesterol itself (loss due to the reduction). The present invention has been accomplished based on these novel findings.

DISCLOSURE OF THE INVENTION

According to the present invention, there is provided a process for preparing high-purity cholesterol, the process comprising selectively reducing the impurities contained in crude cholesterol to cholesterol.

Conventional hydrogenation catalysts can be used for the reduction in the invention. Examples of such catalysts are nickel, platinum, palladium, copper and like metal catalysts, Raney alloy catalysts, copper-chromium oxide and like metallic oxide catalysts, etc.

Usually the reduction reaction of the invention is carried out using starting cholesterol dissolved in a solvent. Examples of useful solvents are solvents which are stable against hydrogenation, such as methyl alcohol, ethyl alcohol, propyl alcohol, isopropyl alcohol and like alcohols, hexane, heptane, cyclohexane and like hydrocarbons, and mixtures of these solvents, etc.

The reaction temperature is variable depending on the type and amount of the catalyst used, type and concentration of the solvent used, reaction time, hydrogen pressure and other factors. The reaction temperature is selected over the range from the lowest temperature at which the catalytic activity is exhibited to the temperature at which dihydrocholesterol is not produced by addition of hydrogen to the double bond in the sterol skeleton. When a Raney nickel catalyst is used, a suitable reaction temperature is about 25° to about 100° C., preferably about 30° to about 60° C.

The hydrogen pressure is variable likewise depending on the reaction temperature, type and amount of the catalyst used, type and concentration of the solvent used and other factors, but usually in the range of about 0.5 to about 10 Kgf/cm$^2$ gauge.

In the practice of the invention, the conditions for the selective reduction reaction can be established according to the following. Under excessively attenuated hydrogenation conditions, the desmosterol remains in a higher ratio. Under excessively intensive hydrogenation conditions, the desmosterol is completely hydrogenated, and the double bond in the skeleton of sterol is also hydrogenated, however, to produce dihydrocholesterol as a by-product. The dihydrocholesterol thus produced as a by-product, however, can be easily removed by recrystallization and poses no particular problem on the purity of the obtained cholesterol. Usually it is desirable that the above-mentioned reduction conditions be established so as to bring the amount of produced dihydrocholesterol to 0.5% or less and the amount of residual desmosterol to 0.3% or less.

It is difficult to directly dry the cholesterol in the solution resulting from the reduction because of its high melting point. Usually the cholesterol is precipitated by crystallization from the solution and is filtered. Thereafter the wet filter cake obtained by filtration is dried. Consequently in the practice of the invention, crystallization is preferably carried out after the reduction to purify the contemplated cholesterol, followed by drying. This is a rational process.

The desmosterol present as a contaminant in usually available cholesterol is structurally different from cholesterol only in the presence of double bond in the 24-position of the side chain. However, according to the invention, the desmosterol can be converted to cholesterol by saturation of double bond of the side chain due to selective reduction, thereby increasing the cholesterol content by 2 to 5% as compared with the starting cholesterol. According to the process of the invention, because the desmosterol which was conventionally difficult to completely remove by recrystallization has been converted to cholesterol by the reduction, lathosterol and other impurities can be readily eliminated only by crystallization subsequent to the selective reduction, whereby cholesterol can be obtained with a high purity and in a high yield.

BEST MODE OF CARRYING OUT THE INVENTION

Examples will be given below to clarify the invention in more detail. The purity of products prepared in Examples was measured by gas-liquid chromatography (GLC) using a device shown below and was calculated as area (%). The percentages indicated refer to the same throughout the specification.

Device: GC-SA (Shimadzu Corp.), detector: FID
Column: Chemical bonded column (GASUKURO KOGYO INC., JARAN)
Liquid phase: SE52 bonded, 0.3 μm-50 m-0.25 mm ID
Temperature conditions: Column temperature:300° C., injection temperature: 330° C.
Detector temperature: 330° C.
Carrier gas: Nitrogen gas, 1 ml/min, spirit ratio: 61:1
Sample: 0.1% heptane solution, 1 μl injected The reduction reaction was conducted using a 500-ml, vertical-type autoclave equipped with an electromagnetic stirrer (Nitto Koatsu Co., Ltd.) operated at 1000 r.p.m. The pressure was measured as gauge pressure. The following abbreviations were used to indicate the results.

|  |  |
|---|---|
| Cholesterol | CHOL |
| Dihydrocholesterol | DHC |
| Desmosterol | DSMO |
| Lathosterol | LATO |

EXAMPLE 1

A reactor was charged with a starting solution of 20 g of commercial cholesterol in 400 ml of normal heptane, and 0.5 g of Raney nickel as a catalyst (NDHT 90, Kawaken Fine Chemical Co., Ltd., calculated as nickel). A hydrogen gas was forced into the reactor so that an initial pressure of 1 kg/cm$^2$ was reached. A reaction was carried out at 50° C. for 1 hour. The catalyst was filtered off after completion of the reaction. A portion of the residue was collected and assayed by GLC. The compositions of cholesterol before and after the reaction are as follows.

|  | CHOL | DHC | DSMO | LATO | Others |
|---|---|---|---|---|---|
| Before reaction | 95.88 | 0.00 | 2.78 | 0.48 | 0.86 |
| After reaction | 99.14 | 0.40 | 0.20 | 0.36 | 0.90 |

EXAMPLE 2

A reactor was charged with a starting solution of 20 g of commercial cholesterol in 400 ml of isopropyl alcohol, and 0.5 g of Raney nickel as a catalyst (NDHT 90, Kawaken Fine Chemical Co., Ltd., calculated as nickel). A hydrogen gas was forced into the reactor so that an initial pressure of 1 kg/cm$^2$ was reached. A reaction was carried out at 30° C. for 1 hour. The catalyst was filtered off after completion of the reaction. A portion of the residue was collected and assayed by GLC. The compositions of cholesterol before and after the reaction are as follows.

|  | CHOL | DHC | DSMO | LATO | Others |
|---|---|---|---|---|---|
| Before reaction | 95.88 | 0.00 | 2.78 | 0.48 | 0.86 |
| After reaction | 98.04 | 0.50 | 0.22 | 0.38 | 0.86 |

EXAMPLE 3

A reactor was charged with a starting solution of 60 g of commercial cholesterol in a solvent mixture of 282 ml of normal heptane and 18 ml of methyl alcohol, and 1 g of Raney nickel as a catalyst (NDHT 90, Kawaken Fine Chemical Co., Ltd., calculated as nickel). A hydrogen gas was forced into the reactor to an initial pressure of 1 kg/cm$^2$. A reaction was carried out at 60° C. for 5 hours. The catalyst was filtered off after completion of the reaction. A portion of the residue was collected and assayed by GLC. The compositions of cholesterol before and after the reaction are as follows.

|  | CHOL | DHC | DSMO | LATO | Others |
|---|---|---|---|---|---|
| Before reaction | 95.88 | 0.00 | 2.78 | 0.48 | 0.86 |
| After reaction | 98.49 | 0.00 | 0.17 | 0.46 | 0.88 |

EXAMPLE 4

The cholesterol specimens were crystallized once from the solutions obtained by the reaction in Examples 1, 2 and 3 with the results shown below. The yields of the cholesterol specimens thus crystallized are also shown. The cholesterol specimens were subjected to confirmatory tests for other properties than the purity, such as a melting point, specific rotation, solubility, etc. The test results show that any of cholesterol specimens met respective ranges specified in the Japanese Pharmacopoeia and in the NF standards, etc.

|  | CHOL | DHC | DSMO | LATO | Others | Yield (%) |
|---|---|---|---|---|---|---|
| Example 1 | 99.38 | 0.00 | 0.00 | 0.21 | 0.41 | 85.0 |
| Example 2 | 99.35 | 0.00 | 0.00 | 0.22 | 0.43 | 85.0 |
| Example 3 | 99.45 | 0.00 | 0.00 | 0.18 | 0.37 | 86.0 |

Comparative Example 1

Recrystallization was carried out three times using commercial cholesterol. The change of composition and the aggregate yield after every recrystallization are shown below.

|  | CHOL | DHC | DSMO | LATO | Others | Yield (%) |
|---|---|---|---|---|---|---|
| Starting cholesterol | 95.48 | 0.00 | 3.32 | 0.38 | 0.82 |  |
| First recrystallization | 97.11 | 0.00 | 2.05 | 0.19 | 0.65 | 65.0 |

-continued

|  | CHOL | DHC | DSMO | LATO | Others | Yield (%) |
|---|---|---|---|---|---|---|
| Second recrystallization | 98.21 | 0.00 | 1.29 | 0.15 | 0.35 | 54.0 |
| Third recrystallization | 98.84 | 0.00 | 0.80 | 0.14 | 0.22 | 42.0 |

Possibility of Industrial Use

According to the invention, cholesterol can be produced with a high purity of at least 98% by a simple reduction procedure and, further by crystallization, can be obtained with a purity of at least 99% and in a high yield of at least 85%. This result can never be achieved in the case of conventional procedure of merely recrystallizing commercial cholesterol.

The high-purity cholesterol obtained by the process of the invention fulfills the requirements in the medical and other fields and is useful as a starting material for synthesis of medicaments and as reagents for biochemical researches.

What we claim is:

1. A method for purifying cholesterol containing desmosterol which comprises selectively reducing the double bond at the C-24 position of desmosterol with hydrogen in the presence of a hydrogenation catalyst.

2. A method for purifying cholesterol containing desmosterol which comprises reducing the desmosterol to cholesterol with hydrogen in the presence of a hydrogenation catalyst.

3. A process for preparing high-purity cholesterol, the process comprising selectively reducing the double bond at the 24-position of the side chain of desmosterol contained in crude cholesterol to cholesterol, said reduction being conducted under such conditions that the amount of produced dehydrocholesterol is to be brought to 0.5% or less and the amount of residual desmosterol is to be brought to 0.3% or less.

* * * * *